United States Patent [19]
Reddy

[11] 3,938,075
[45] Feb. 10, 1976

[54] EXHAUST GAS SENSOR FAILURE DETECTION SYSTEM

[75] Inventor: Junuthula Nirdosh Reddy, Troy, Mich.

[73] Assignee: The Bendix Corporation, Southfield, Mich.

[22] Filed: Sept. 30, 1974

[21] Appl. No.: 510,277

[52] U.S. Cl............. 340/52 R; 340/237 R; 431/75; 60/285
[51] Int. Cl.² ........................................ G08B 21/00
[58] Field of Search ........ 340/52 R, 52 D, 52 F, 53, 340/236, 237 R, 237 S; 431/75, 76; 60/276, 285

[56] References Cited
UNITED STATES PATENTS

3,788,124  1/1974  Teton.......................... 340/237 R X

*Primary Examiner*—Alvin H. Waring
*Attorney, Agent, or Firm*—Russel C. Wells

[57] ABSTRACT

In a fuel management system of an internal combustion engine having an exhaust gas sensor positioned in the exhaust gases of the engine for controlling the fuel mixture to the engine, an exhaust gas sensor failure detection system for determining when the sensor fails to respond within a given time period to a rich to lean fuel mixture transition. The sensor in response to a rich fuel mixture generates a high voltage output which is switched to a low voltage output when the fuel mixture goes lean. The time of transition is used as an indication of the quality and performance of the exhaust gas sensor.

10 Claims, 6 Drawing Figures

FIG. 6

EXHAUST GAS SENSOR FAILURE DETECTION SYSTEM

BACKGROUND OF THE INVENTION

1. Field of the Invention

This invention relates to exhaust gas sensors as used in the control of the air and fuel mixture in an internal combustion engine and more particularly to a system for the detection of the failure of such an exhaust gas sensor.

2. Description of the Prior Art

The use of an exhaust gas sensor in exhaust systems of internal combustion engines for controlling the air/fuel ratio to the engine is well known as exhibited in the U.S. Pat. No. 3,745,768 issued to Zechnall et al. and entitled "Apparatus To Control The Proportion Of Air and Fuel In The Air/Fuel Mixture of Internal Combustion Engines." In this particular patent an oxygen analyzer or exhaust gas sensor is responsive to the oxygen present in the exhaust gas of an internal combustion engine. A signal is generated by the sensor indicating whether or not oxygen is present in the exhaust gas and this signal is supplied to an electronic control unit for controlling or supplying information to control the amount of fuel injected into the cylinder of the internal combustion engine. If the sensor indicates that oxygen is present in the exhaust gas the sensor signal will supply information to the control unit to increase the amount of fuel supplied to the internal combustion engine. Conversely, if the sensor indicates a lack of oxygen in the exhaust gas it will supply information tending to reduce the amount of fuel supplied to the cylinder.

Such control is necessary for an internal combustion engine to improve the performance of the engine and to control the quality of the exhaust gas components in the exhaust gas of an internal combustion engine.

The use of exhaust gas sensors in the exhaust lines of furnaces is likewise old in the art. Again the purpose of such sensors in the exhaust lines is to control the operation of the furnace for better performance and economy.

Oxygen sensors are used in the steel making processes to determine the amount of oxygen contained in the molten steel in the process of manufacture. These sensors generate signals which are applied to a control unit to control the process in the steel making.

In such instances of the prior art, detection of a failed sensor has been primarily one of observation by an operator such as by the ultimate failure of a component such as a converter downstream of the sensor or the physical destruction of the sensor by the environment in which it is placed. Constant or periodic monitoring of the output voltage of the sensor under controlled conditions has been required in order to determine whether or not the sensor is operating or performing correctly.

In fuel management systems for internal combustion engines it is necessary to accurately control the fuel/air ratio entering the engine in order to control the products of combustion as they appear in the exhaust gases. It is desired in the exhaust gas of internal combustion engines to control the amount of unburnt hydrocarbons and carbon monoxides by regulating the fuel/air mixture to the cylinder of the engine. Nitrogen compounds in the exhaust gases are another undesirable component which may be neutralized by a catalytic converter placed downstream of the gas sensor. With the gas sensor controlling the fuel/air ratio into the engine thereby controlling hydrocarbons and carbon monoxide in the exhaust gas the catalytic converter need only have a single bed for neutralizing nitrogen compounds.

SUMMARY OF THE INVENTION

The invention comprises an exhaust gas sensor such as an oxygen gas sensor positioned in the exhaust gas of an internal combustion engine for generating either one or two voltage levels in response to the presence or absence of oxygen in the exhaust gas. The output of the sensor is electrically connected to a pair of comparators whose outputs depend on the sensor voltage output being below two predetermined voltage threshold levels. These two threshold levels are indication of a proper sensor voltage operation. The system responds to the transition of the sensor from one threshold level to a second threshold level in response to the oxygen mixture of the exhaust gas passing by the sensor.

It is a principal object of this invention to detect the failure of an exhaust gas sensor in the exhaust gas system of an internal combustion engine.

It is another object of this invention to provide a system for detecting the quality of production of exhaust gas sensors prior to their installation in conjunction with internal combustion engines.

It is yet another object of this invention to provide a continuous warning to the operator of an internal combustion engine when an exhaust gas sensor has failed and thereby permitting proper servicing steps to be maintained.

It is a further object of this invention to detect a failure exhaust gas sensor without requiring specific engine operating conditions other than determination that the sensor is at its operating temperature.

It is an indication of the quality of the sensor when the transition from the high voltage level to a low voltage level takes place within a predetermined interval as the exhaust gas is changed from a rich fuel mixture to a lean fuel mixture. If within a given period of time the sensor fails to make this transition within the predetermined interval, this is an indication of the failed sensor and the circuitry electrically connected thereto will provide a warning to the operator. A capacitor is electrically connected for charging to the output of the first comparator for storing an electrical signal representing the time duration of the output of the first comparator. A first timing generating means is responsive to the output of the first comparator for generating a timing signal for testing the output of the second comparator. If the output of the second comparator occurs during the timing signal duration, a storage reset means is activated for discharging the capacitor.

If however the second comparator does not have an output within the timing signal duration, the capacitor continues to charge in response to the output of the first comparator.

If the charge on the comparator reaches a predetermined voltage level within a predetermined time as determined by a voltage level from a timing voltage reference means, the third comparator generates an output which is supplied to a warning system for warning the operator of the engine that the sensor has failed.

DETAILED DESCRIPTION

Figure 1:
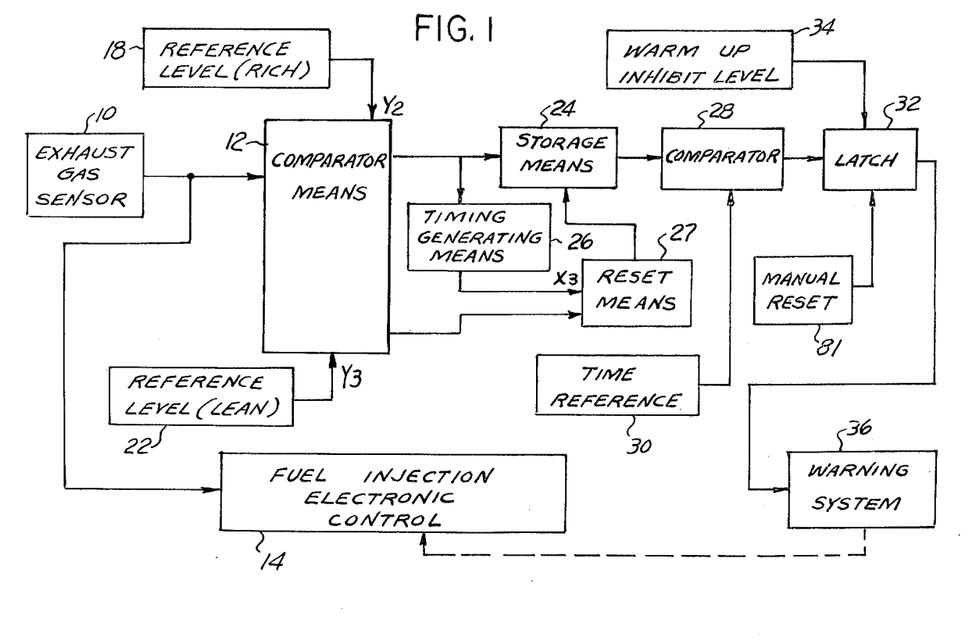
FIG. 1 is a block diagrammatic schematic of an exhaust gas sensor failure detection system.

Referring to the FIGS. by the characters of reference there is illustrated in FIG. 1 a block diagrammatic schematic of the exhaust gas sensor failure detection system according to the present invention.

The exhaust gas sensor 10 is positioned in the exhaust gas conduit of the internal combustion engine. The sensor is responsive to one of the constituent gases of combustion. The sensor will generate a first electrical signal greater than a first voltage threshold level in the presence of a first fuel mixture and will generate a second electrical signal less than a second voltage threshold level in the presence of a second fuel mixture.

For the purposes of this disclosure, one particular embodiment of exhaust gas sensors is an oxygen gas sensor of the class of sensors which may be used in a fuel management system for an internal combustion engine. The purpose of the sensor is to sense a particular characteristic or performance or result of the operation of an internal combustion engine and generate an electrical signal in response thereto.

In the preferred embodiment the sensor used in an oxygen gas sensor which is positioned in the exhaust system of the internal combustion engine and senses the presence or absence of oxygen gas in the exhaust gas. If the oxygen gas sensor senses oxygen in the exhaust this is defined as resulting from a lean fuel mixture being supplied to the engine and conversely if the sensor detects a lack of oxygen gas in the exhaust this is defined as resulting from a rich fuel mixture being supplied to the internal combustion engine. The voltage level of the output signal of the $O_2$ sensor in a rich fuel mixture condition is approximately 800 millivolts and the voltage level of the output signal of the sensor in a lean fuel mixture condition is approximately 75 millivolts. For the purposes of this disclosure the electrical signal output of the sensor is high in a first or rich fuel mixture and low in a second or lean fuel mixture.

As illustrated in FIG. 1, the output of the $O_2$ sensor 10 is supplied in a substantially parallel manner to a comparator means 12 and to the fuel injection electronic control unit 14. The fuel injection electronic control unit 14 contains all the logic and circuitry necessary for controlling the fuel management system of the internal combustion engine.

The comparator means 12 further comprises a first comparator 16 to which is supplied a first voltage threshold level 18 for a rich fuel mixture and a second comparator 20 to which is supplied a second voltage threshold voltage level 22 representing a lean fuel mixture. The outputs of both comparators 16 and 20 are supplied to a storage means 24 wherein the first output signal from the first comparator 16 is stored as a variable voltage level proportional to the amount of time that the sensor 10 stays below the rich reference voltage level. When the sensor output voltage goes below the second threshold voltage level within a predetermined interval as defined by a timing generating means 26, the storage reset means 27 operates to clear the stored signal.

The output signal of the storage means 24 is supplied to a third comparator 28 wherein the signal is compared to a timing voltage signal from a timing voltage reference means 30 which is proportional to the maximum allowable time between successive reset signals. The comparator 28 generates an output signal in response to simultaneous occurrence of the timing voltage signal from the timing voltage reference means 30 and a predetermined voltage level from the storage means 24.

The output signal from the third comparator 28 is supplied to an alarm means or a latching circuit means 32 which is conditional by means of an inhibit means 34 for operation upon the engine being at a particular operating condition, namely, warmed up. When the latching circuit means 32 operates it generates and maintains an error signal which is supplied to a warning system 36. The warning system 36 receives the signal from the latching circuit means 32 and indicates to the operator of the internal combustion engine by any one or a combination of several different warning alarms, the information that the sensor 10 is malfunctioning. Examples of such warning systems 36 are lights, buzzers, or other systems controlling the operation of the engine whereby the operator will have to provide service for the sensor.

As previously indicated the exhaust gas sensor 10 may be an oxygen gas sensor that switches between high and low voltage levels as the oxygen content of the exhaust gas changes. The switching point for the oxygen gas sensor is at an air/fuel ratio representing stoichiometric chemical operation. At stoichiometric which is an air/fuel ratio of approximately 14.8:1, the output of the sensor is rapidly switched between its high and low levels.

As the sensor 10 decays or ages in time, the switching time between the two levels increases to such an extent that under rapid engine operations the sensor may not follow the composition of the exhaust gas. It is an object of this invention to use the switching rate of the sensor as an indication of the quality of the sensor, thereby, once the sensor signal crosses the first voltage threshold level in response to a rich to lean exhaust gas change, the sensor must complete the transition to the second voltage threshold reference level within a predetermined time period or interval. If the sensor 10 does not complete this transition within this predetermined interval, this may be an indication of a bad sensor.

Figure 2:
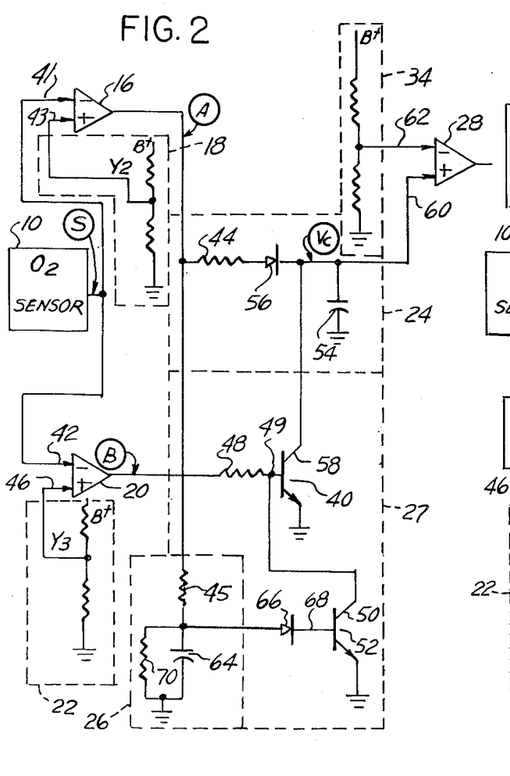
FIG. 2 is an electrical schematic of a preferred embodiment of the circuitry of FIG. 1.
Figure 3:
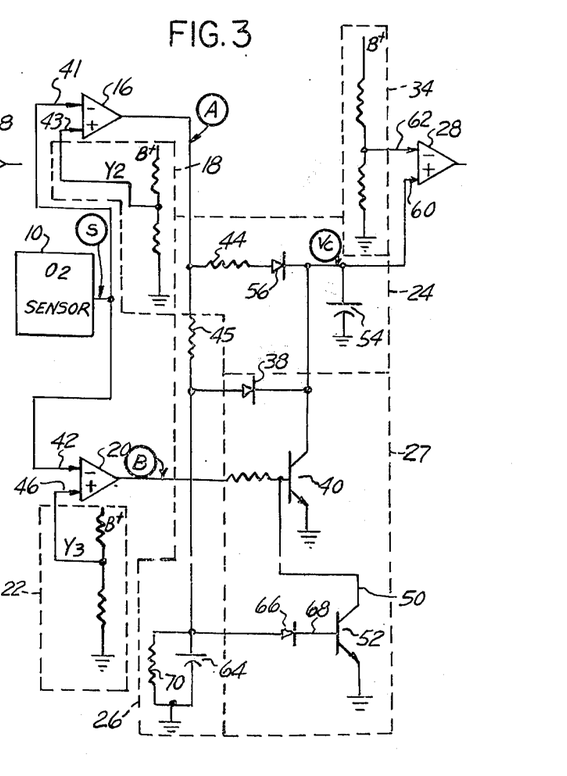
FIG. 3 is an electrical schematic of an alternate embodiment of the circuit of FIG. 1.

Referring to FIGS. 2 and 3, which are substantially identical circuits with the exception of a clamping means or diode 38 between the collector of the first or reset transistor 40 and the output of the timing generating means 26. The purpose and function of this diode 38 will be better explained after the general operation of the circuit is understood.

Referring to FIG. 2, there is illustrated the sensor 10 with its output electrically connected to the inverting inputs 41 and 42 of the first and second comparators 16 and 20 of the comparator means. The noninverting input 43 of the first comparator 16 is electrically connected to the first voltage reference circuit 18 which generates a first voltage threshold $Y_2$ which is equal to the minimum acceptable voltage level from the sensor 10 in the presence of a first or rich fuel mixture. In the preferred embodiment $Y_2$ is equal to 600 millivolts. The output of the first comparator 16 is high when the voltage input on the inverting input 41 is less than the voltage value $Y_2$. The output voltage level from the first comparator 16 is supplied to a pair of resistors 44 and 45, the first resistor 44 being electrically connected in series to the storage means 24 and the second resistor 45 being electrically connected in the timing generating means 26.

The output of the sensor 10 is additionally electrically connected to the inverting input 42 of the second comparator 20 of the comparator means 12. The noninverting input 46 of the second comparator 20 is electrically connected to a second voltage reference circuit 22 for generating a second voltage threshold $Y_3$ which is equal to the maximum acceptable voltage level output of the sensor 10 in the presence of a second or lean fuel mixture. A good or operating sensor 10 operating in a lean fuel mixture exhaust gas has output voltage substantially less than the second voltage threshold $Y_3$ which is 300 millivolts in the preferred embodiment. In a manner similar to the first comparator 16 the output of the second comparator 20 is a high voltage level when the voltage input on the inverting input 42 is less than $Y_3$. The output of the second comparator 20 is electrically connected through a resistor 48 to the base 49 of the reset transistor 40 and to the collector 50 of the second or timing transistor 52.

The storage means 24 in the preferred embodiment comprises a capacitor 54 which is charged to the voltage output generated by the first comparator 16 through the first resistor 44 and an isolation diode 56. The one plate of the storage capacitor 54 is electrically connected to the cathode of the isolation diode 56, the collector 58 of the reset transistor 40 and the noninverting input 60 of the third comparator 28. The inverting input 62 of the third comparator 28 is electrically connected to a timing voltage reference means 34 or voltage divider network wherein the voltage applied to the inverting input 62 is a level which corresponds to a substantially long time period. In essence, the time period represented by this voltage level is used to determine whether or not the sensor 10 has failed. The output of the third comparator 28 is high when the voltage level at the noninverting input 60 from the charge on the storage capacitor 54 exceeds the voltage level of the voltage divider 34. As will hereinafter be shown, this high voltage level of the output of the third comparator 28 is an indication of an inoperative or failed sensor 10.

The one plate of the storage capacitor 54 as previously indicated is electrically connected to the collector 58 of the reset transistor 40. When the reset transistor 40 is driven into conduction it provides a rapid discharge path for the storage capacitor 54 for the purpose of discharging or clearing the storage means 24 and reinitiating the testing of the sensor 10.

The reset transistor 40 has its base 49 electrically connected through a resistor 48 to the output of the second comparator 20 and is conditionally responsive to the output of the second comparator 20. If the output of the second comparator 20 is high, the reset transistor 40 may be driven into conduction provided the timing transistor 52 connected to its base 49 is out of conduction.

The timing generating means 26 comprises the second or timing resistor 45 and a series timing capacitor 64 electrically connected between the output of the first comparator 16 and ground. The junction between the timing resistor 45 and the capacitor 64 is electrically connected through a diode 66 to the base 68 of the timing transistor 52. Additionally a discharge resistor 70 is electrically connected in shunt with the timing capacitor 69. When the output of the first comparator 16 is high the timing capacitor charges to a voltage value, equal to two diode voltage drops, sufficient to supply enough base current to turn on the timing transistor 52. When the timing transistor 52 is turned on, the base of the reset transistor 40 is clamped to ground preventing the reset transistor 40 from being driven into conduction. However, if the reset transistor 40 is in conduction, it is driven out of conduction. When the output of the first comparator 16 is low, the timing capacitor 64 discharges through its shunt resistor 70 and turns off the timing transistor 52.

In FIG. 3 there is the addition of the clamping diode 38 electrically connected between the collector 58 of the reset transistor 40 and the timing capacitor 64. The function of this diode 38 is to clamp the output of the timing capacitor 64 at ground through the reset transistor 40 when the reset transistor is driven into conduction prior to the timing transistor 52 being driven into conduction. With this diode 38 electrically connected in the circuit once the reset transistor 40 is turned on by the output of the second comparator 20, it will not be influenced by the output of the first comparator 16. This will be made clear with reference to the timing diagrams of FIGS. 4, 5, and 6.

OPERATION

It was previously indicated that the purpose of the system of FIG. 1 is to detect a failure in a sensor 10 such as an oxygen gas sensor. Once the failure is detected the circuit will generate a signal which may be used in many ways to indicate the failure of the sensor 10 to the engine operator. However, as previously indicated, this is also an object of the invention to provide failure detection systems which may be used for production monitoring during the manufacture of exhaust gas sensors.

As previously indicated when the sensor environment is switched from a rich to lean gas mixture, the sensor 10 output switches from a high to a low voltage level. Such a sensor may be considered to have failed if the response of the switching is slower than a predetermined time which will be defined by the timing generating means 26 comprising the series resistor 45 and the timing capacitor 64, and the second or timing transistor 52.

The sensor 10 is also considered to have failed if it remains at the low voltage level for a period of time which is substantially long compared to the switching time. This is an example of a broken sensor wherein its output voltage remains low and is uneffected by the quality of the exhaust gas passing thereby.

Figure 6:
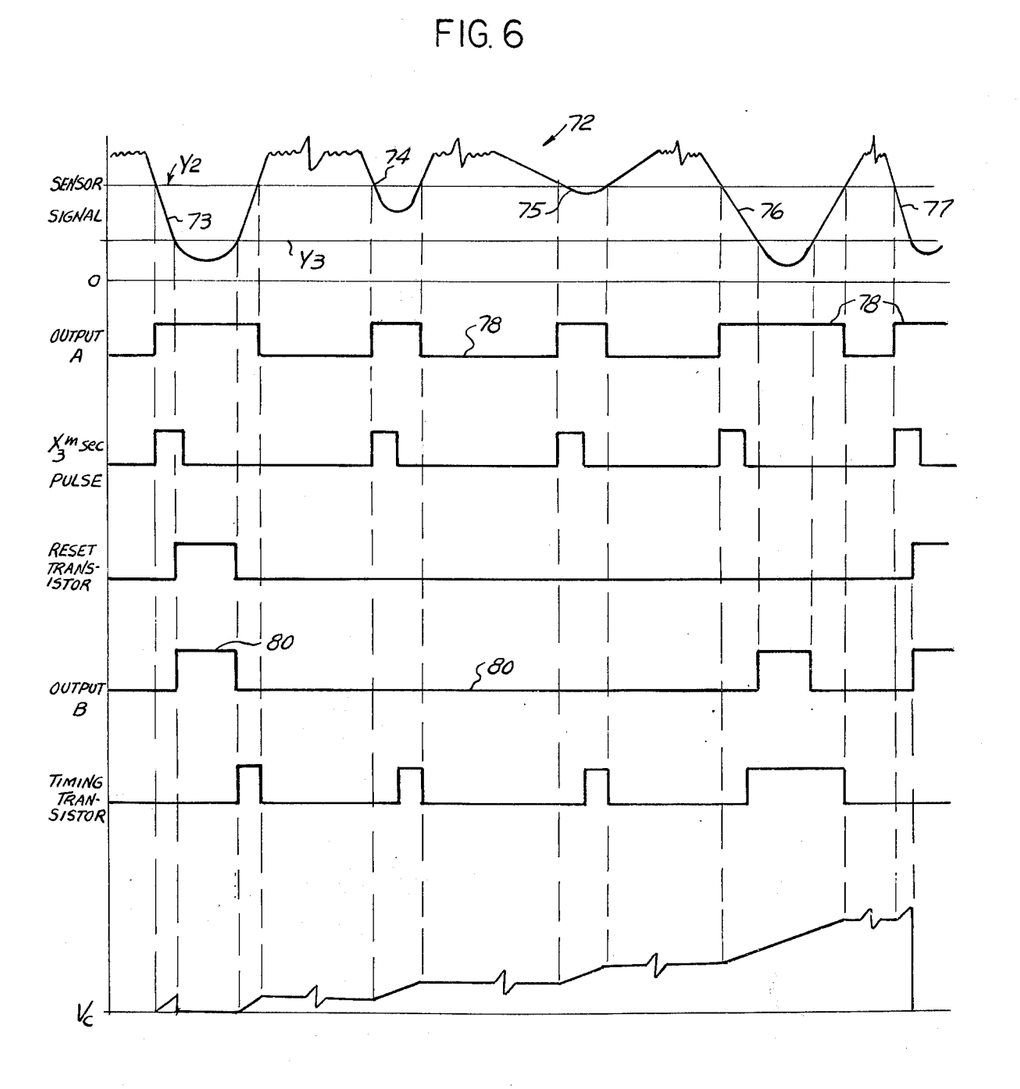
FIG. 6 is a diagram showing the waveshapes of the signal of several points of the schematic illustrated in FIG. 3.

Referring to FIG. 6, the upper waveform 72 represents the voltage waveform of a typical oxygen gas sensor 10 responding to the exhaust gas as a result of several changes in the air/fuel mixture supplied to the internal combustion engine. This waveform illustrates the waveshape of five possible voltage waveshapes 73–77 from the oxygen gas sensor 10 in response to the exhaust gas. The first waveshape 73 is a waveshape of a good sensor, wherein the transition from rich to lean is within the defined interval as defined by the circuitry. The second waveshape 74 to the right, illustrates the output of the sensor 10 responding to a very fast change between rich, lean, and back to rich condition of the exhaust gas. The third waveshape 75 represents another sensor signal generated in response to the slow switching transition between a rich and lean exhaust gas and in fact the sensor fails to respond to the lean mixture. The fourth waveshape 76 represents a sensor characteristic which would not be acceptable in that the switching transition is extremely long. The fifth waveshape 77 represents a sensor responding to the switching between rich and lean fuel mixtures in an acceptable interval.

By following the sensor waveshapes of FIG. 6, the circuit of FIG. 3 is easily understood. The circuit is defined so that the time of transition from first voltage threshold level $Y_2$ to the second voltage threshold level $Y_3$ must occur within a time period defined by $X_3$. This time period $X_3$ is generated by the timing generating means 26 and operates to turn on the second or timing transistor 52. As illustrated in the sensor waveshape 72, as the sensor signal crosses the $Y_2$ threshold, the output of the first comparator 16 is driven high. This first comparator 16 will maintain its output as long as the sensor signal is below the threshold level $Y_2$. Simultaneously, the output signal 78 from the first comparator 16 is supplied to both the capacitor 54 through the resistor 44 and isolation diode 56 and to the timing generating means 26.

The capacitor 54 in the timing generating means 26 must charge through its timing resistor 45 to a voltage having a magnitude sufficient to turn on the timing transistor 52. In FIG. 3, this voltage is equivalent to two diode voltage drops above ground. The first voltage drop is that of the series diode 66 connected in the base 68 of the transistor 52 and the second voltage drop is due to the base-emitter junction. The time of the timing generating means 26 is represented by the width of the pulse $X_3$ in FIG. 6. In FIG. 6, the waveshape Vc illustrates the charging of the capacitor 54 by the voltage output of the first comparator 16. As the sensor output crosses the threshold level $Y_3$ in FIG. 6, the output of the second comparator 20 goes high as illustrated in the signal waveform 80. When this voltage goes high, during the time period $X_3$, the reset transistor 40 is turned on and through the clamping diode 38, the timing generating means capacitor 64 is clamped through the collector emitter junction of the reset transistor 40. This prevents the timing transistor 52 from going into conduction and thereby allows the reset transistor 40 to discharge the capacitor 54.

When the fuel mixture switches from a lean to a rich mixture the voltage output of the sensor crosses the threshold $Y_3$ causing the output signal 80 of the second comparator 20 to go low. With this output low, the reset transistor 40 is driven out of conduction. The output of the first comparator 16 is then applied to the storage means 24 which begins to apply a charge to the storage capacitor 54. The timing generating means 26 is again initiated and depending on the rise time of the sensor 10, the timing transistor 52 may or may not be driven into conduction. However, since the output of the second comparator 20 is low and will remain low, the timing transistor 52 has no effect on the operation of the reset transistor 40 at this time.

When the sensor output voltage crosses the threshold $Y_2$ the output of the first comparator 16 is turned off, removing the charging power for the storage means 24 from the circuit. The timing capacitor 64 then discharges through its shunt resistor 70 for conditioning the circuit for the next sensor output voltage swing.

Referring to the second sensor waveshape 74, it is shown that the sensor output crosses the threshold $Y_2$ but does not cross the threshold $Y_3$ and quickly returns back across the threshold $Y_2$. This is an indication of the exhaust gases being basically rich, except for a short quantity of gas which was lean. In this example, the output of the first comparator 16 is driven high for the total time at the sensor, is below the threshold $Y_2$ and in addition the timing generating means 26 will generate or begin to time out and may or may not drive the timing transistor 52 into conduction. The decision of whether or not the timing transistor 52 is driven into conduction is based on the time length of the output signal from the first comparator 16. However, in this situation, the first comparator 16 does supply energy to the storage means 24 for increasing the voltage level on the capacitor 54.

The third sensor signal waveshape 75 is similar to the second with the exception of the slope being much more gradual or slower. The end result is that the storage capacitor 54 is charged up to a higher level as illustrated in the Vc waveshape.

The fourth sensor signal waveshape 76 is an illustration wherein the slope or transition time for the sensor to cross both thresholds, $Y_2$ and $Y_3$ is greater than that allowed by the timing generating means and the net result is that the timing transistor 52 is driven into conduction to prevent the reset transistor 40 from being driven into conduction by the output from the second comparator 20. The net result is that the output of the first comparator 16 is applied to the storage means 24 and increases the charge thereon.

Referring to the fifth sensor signal waveshape 77, which is similar to the first waveshape, in that the transition from the threshold level $Y_2$ to $Y_3$ being within the predetermined time allowed by the timing generating means 26. The net effect is the turning on of the reset transistor 40 completely discharging from the storage means 24 and the diode 38 operates to clamp the timing generating means 26 and to effectively discharge the timing capacitor 64.

Figure 5:
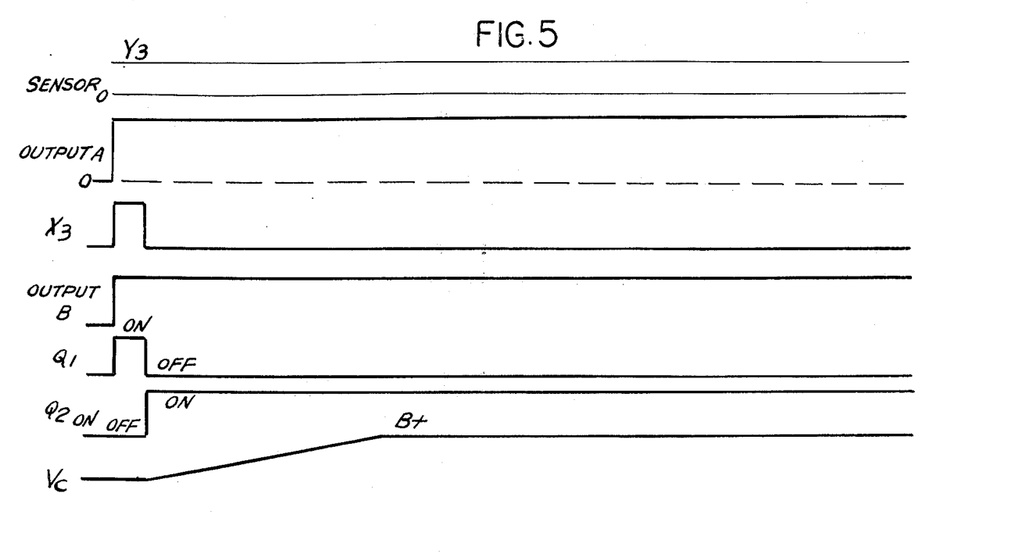
FIG. 5 is a diagram showing the waveshapes of the signal of several points of the schematic illustrated in FIG. 2 with the sensor broken.

It was previously indicated that the difference between the embodiment of FIG. 3 and the embodiment of FIG. 2 is in the addition in FIG. 3 of the diode 38 clamping the timing generating means 26 to the collector 58 of the reset transistor 40. Without this diode 38 as illustrated in FIG. 2, the circuit will detect a broken sensor which would generate a low or zero voltage output as represented in FIG. 5 wherein the waveshapes are similar to those of FIG. 6. If the sensor is broken, the output of the first 16 and second comparators 20 are both high. The output of the second comparator 20 will turn on the reset transistor 40 effectively shorting the charging voltage to the storage means 24 from the first comparator 16. However, the timing generating means 26 will begin to time out as a result of the output from the first comparator 16, and the second transistor 52 will eventually turn on at the end of time $X_3$. Turning on the timing transistor 52 removes the signal from the base of the reset transistor 40 driving it out of conduction and allowing the output signal from the first comparator 16 to charge the storage means 24. The charge voltage on the storage means 24 will then charge up to the output voltage level of the first comparator 16.

Figure 4:
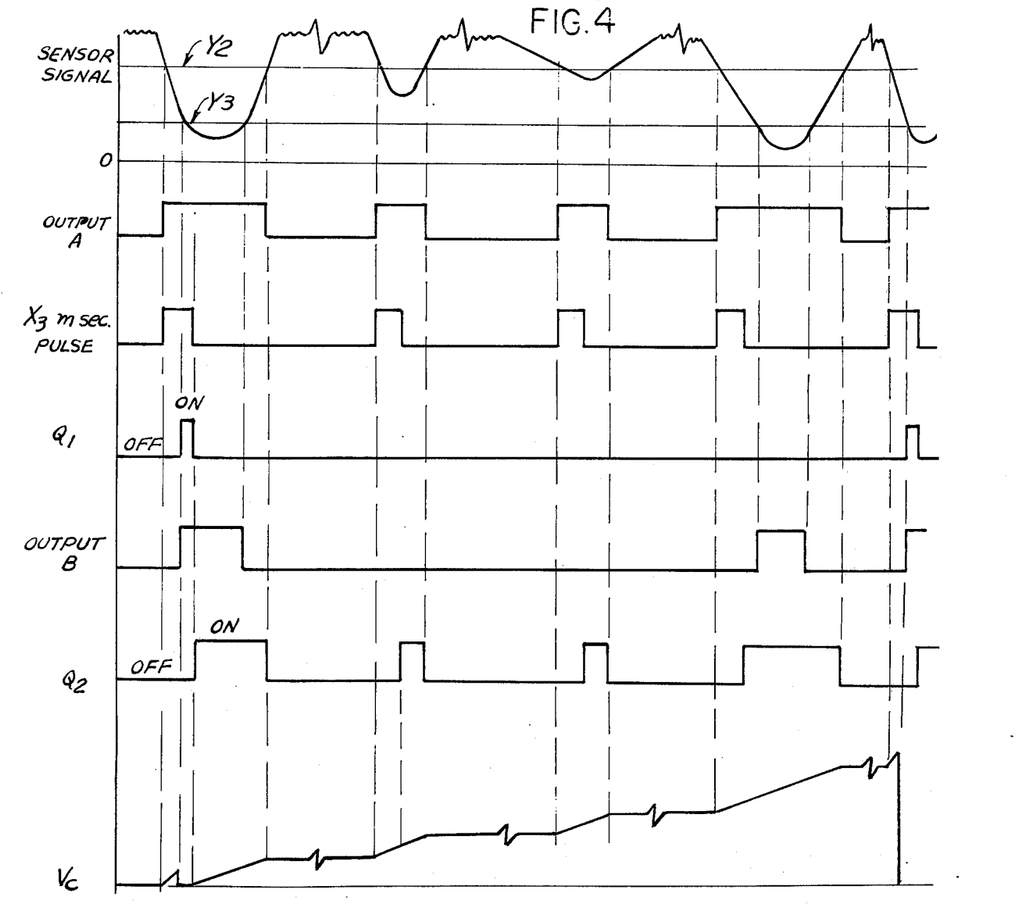
FIG. 4 is a diagram showing the waveshapes of the signals of several points of the schematic illustrated in FIG. 2.

FIG. 4 illustrates the voltage waveshapes for the circuit of FIG. 2 under the same conditions as previously explained in connection with FIG. 6 and FIG. 3.

Regardless of which circuit configuration is used, that is circuit configuration of FIG. 2 or FIG. 3, the output voltage of the storage means 24 is applied to the noninverting input 60 of the third comparator 28. As previously indicated the voltage level applied to the inverting input 62 of the third comparator 28 is from a voltage divider network 34 and the voltage level represents a time interval during which the $O_2$ sensor should make a valid transition from rich to lean exhaust gas conditions. If the voltage on the storage capacitor 54 exceeds this level the output of the third comparator 28 becomes a high level and is supplied to the latching means 32.

As illustrated in FIG. 1, the latching means 32 is conditioned by an inhibit signal 34 which may represent any inhibiting condition. In the preferred embodiment this signal is identified as warm up inhibit and is a signal which may be generated from a temperature transducer in response to engine coolant temperature. The function of the warm up inhibit circuit 34 is to insure that the sensor 10 is at its operating temperature and is generating the proper voltage level output signals before the sensor failure detection systems tests its characteristics. Also as indicated in FIG. 1, there is means 81 applied to the latching means 32 for manually resetting the latching means. Such manual resetting is optional and is not considered necessary for the operation of the sensor failure detection system of FIG. 1.

An example of such latching means 32 may well be conventional bistable multivibrator wherein the warm up inhibit signal is applied to the clearing or reset side of a multivibrator and effectively holds the multivibrator in a reset state, during a period of time that the signal is present. Once the engine has warmed up, the inhibit signal is driven low and the multivibrator is responsive to any high output voltage from the third comparator. Once the multivibrator is set, it will remain set until power is removed from the system or a resetting signal is applied to the reset side of the flip-flop.

The output of the latching means 32 indicated in FIG. 1 will drive or supply a signal to some form of warning system 36 which may be a light in the operator's compartment which will illuminate when the multivibrator is in its true or set state. An additional warning system 36 may be a buzzer in the operator's compartment which when the flip-flop is in its true or set state will sound the alarm thereby indicating to the operator that the sensor has failed but yet during normal engine operating conditions the warning system does not effect the engine operation in such a manner to disable the vehicle.

During the manufacturing of exhaust gas sensors for use in exhaust systems of internal combustion engines, the sensor may be tested prior to its being positioned in an internal combustion engine system. In a preferred embodiment using an oxygen gas sensor, the sensor is responsive to an atmosphere changing between a reducing atmosphere or one of no oxygen to an oxidizing atmosphere or one containing oxygen gas. In the manufacturing of the sensors it is necessary to position the sensor into a stream of gas having a chemical balance which is controlled. Electrically connected to the output of the sensor are means for measuring the voltage level of the output of the sensor as the chemical balance of the gas passing by the sensor is changed from a reducing to an oxidizing atmosphere. When the measured level of the voltage output of the sensor falls below the first predetermined voltage threshold level the timing is started or initiated. When the voltage output of the sensor responding to the oxidizing atmosphere crosses the second voltage threshold level, the timing is terminated and its indicated interval is measured. This interval is then compared to a predetermined time interval and if the interval is less than a predetermined time interval the sensor is found to be acceptable. However, if the measured interval is greater than a predetermined time interval, this indicates a failed sensor and the sensor is rejected from production.

In determining the quality of exhaust gas sensors after their fabrication and prior to their commercial use, it is necessary to place the sensor in a gas atmosphere containing the gas to be measured. In response to a first gas mixture containing the gas to be measured the sensor will generate a voltage signal having an amplitude greater than a first predetermined voltage threshold signal. The gas atmosphere is then changed to a second gas mixture wherein the gas to be measured is removed and the sensor should then generate a second voltage signal having an amplitude less than a predetermined second voltage threshold signal.

Upon determining that the sensor has these two voltage signal characteristics the gas is then returned to the first gas mixture composition. The output voltage of the sensor is compared with the first predetermined voltage threshold level and, as the gas mixture is changed, the first voltage signal is generated when the voltage output of the sensor is equal to said first predetermined voltage threshold. This first voltage signal is maintained during the period of time when the voltage output of the sensor is less than this first predetermined voltage threshold signal. The gas mixture is then changed to the second gas mixture and the voltage output of the sensor is compared with the second predetermined voltage threshold signal. When the voltage output of the sensor is equal to the second voltage threshold signal the second voltage signal is generated and maintained during the period of time when the sensor voltage is less than the second predetermined voltage threshold signal.

The first voltage signal is stored as a varying third voltage signal wherein the amplitude of the third voltage signal is in proportion to the time duration of said first voltage signal. In addition to the first voltage signal being stored, a timing signal is generated from the leading edge of the first voltage signal. This timing signal has a predetermined timing interval during which time a quality gas sensor will have generated a voltage which is equal to the second threshold signal, thereby generating the second voltage signal. Comparing the coincidence of the timing signal with the second voltage signal and if coincidence is found the stored third voltage signal is clear. If coincidence is not found between the timing signal and the second voltage signal, an alarm is generated indicating that the quality of the gas sensor may not be that which it is desired.

A less strict quality testing of the manufactured gas sensor can be performed by having the gas mixture continuously cycled between the first and second mixtures and each time the voltage output of the sensor causes the first voltage signal to be generated this signal is stored as the third voltage signal. When the third voltage signal reaches a predetermined voltage magnitude between successive storage reset signals or before a storage reset signal is generated, this is an indication that the sensor is not operating correctly and should be rejected.

There has thus been shown and described a sensor failure detection system for sensing the failure of any type of sensor connected to a fuel management system for an internal combustion engine. Particularly the system illustrated detects the failure of an oxygen gas sensor in the exhaust system of an internal combustion engine and will generate a warning to the operator of the failure of such a sensor. Additionally there is described a means for testing the sensor in a production or manufacturing environment.

I claim:

1. In a fuel management system for an internal combustion engine wherein the quality of combustion of the fuel is sensed by a sensor unit in the exhaust gas, a sensor detection system comprising:

an exhaust gas sensor positioned in the exhaust gas conduit of the internal combustion engine, said sensor responsive to one of the constituent gases of combustion for generating a first electrical signal greater than a first voltage threshold level indicating a first fuel mixture and generating a second electrical signal less than a second voltage threshold level indicating a second fuel mixture;

comparator means responsive to said sensor for generating a first output signal when said first electrical signal falls below and remains below said first voltage threshold level and for generating a second output signal when said second electrical signal falls below and remains below said second voltage threshold level;

storage means responsive to said first output signal from said comparator means for storing an electrical signal during the time duration of said first output signal;

timing generating means responsive to the leading edge of said first output signal for generating a timing signal having a predetermined interval;

storage reset means responsive to the simultaneous occurrence of said timing signal and said second output signal for generating a reset signal for clearing said storage means;

a timing voltage reference means for generating a voltage level representing an interval substantially greater than said first interval, and a comparator for receiving said signal from said timing voltage reference means and said electrical signal from said storage means and generating an ouput signal when the magnitude of said electrical signal exceeds the magnitude of said voltage level from said timing voltage reference means.

2. The sensor detection system according to claim 1 additionally including:

a conditional circuit means responsive to a predetermined condition for generating a signal whenever said predetermined condition is present, and a latching circuit means for receiving the said output signal from said comparator and said signal from said conditional circuit means for generating a retaining signal upon the simultaneous occurrence of both of said signals.

3. The sensor detection system according to claim 1 additionally including an alarm means responsive to said output signal from said comparator.

4. The sensor detection system according to claim 1 wherein said sensor is an oxygen gas measuring sensor generating a high voltage output signal above said first threshold level when the gas flowing relative thereto is in a reducing state and generates a voltage output signal below said second threshold level when the gas flowing relative thereto is in an oxidizing state.

5. The sensor detection system according to claim 1 wherein said storage means comprises a capacitor electrically connected for receiving said first output signal from said comparator means and wherein the voltage charge level of the electrical signal on said capacitor is proportional to the total time duration of the occurrences of said first output signals between successive reset signals from said storage reset means.

6. The sensor detection system according to claim 5 wherein said storage reset means comprises:

a first transistor having its input and output leads electrically connected in circuit for discharging said capacitor, said control lead of said transistor adapted to receive said second output signal from said comparator means for discharging said capacitor, and a second transistor having its input and output leads electrically connected in shunt between said control lead and said output lead of said first transistor, the control lead of said second transistor adapted to receive said timing signal from said first timing generating means for driving said second transistor into conduction after said predetermined interval of said timing signal for holding said first transistor out of conduction.

7. The sensor detection system according to claim 6 additionally including:

a clamping means electrically connected between the input lead of said first transistor and said timing generating means for limiting the amplitude of the signal on said timing generating means to the amplitude of the signal on said input lead for clamping said second transistor out of conduction when said first transistor is driven into conduction.

8. A method for determining the quality of a gas sensor responsive to an atmosphere changing between a reducing atmosphere and an oxidizing atmosphere wherein the gas sensor generates an electrical signal having a first voltage level in the presence of the reducing atmosphere and a second voltage level in the presence of an oxidizing atmosphere, said method comprising the steps of:

positioning the sensor into a stream of gas, changing the chemical balance of the gas between a reducing atmosphere and an oxidizing atmosphere, measuring the voltage level output of the sensor in both the reducing gas and the oxidizing gas, initiating timing when the voltage level of the electrical signal of the sensor goes below a first predetermined voltage threshold level when the atmosphere is changed from a reducing atmosphere to an oxidizing atmosphere, terminating the timing when the voltage level of the electrical signal of the sensor goes below a second predetermined voltage threshold level, comparing elapsed time with a predetermined time interval, and selecting the sensor having an elapsed time less than the predetermined time interval.

9. A method for measuring the quality of gas sensors responsive to a first fuel mixture for generating a voltage signal having an amplitude greater than a predetermined first voltage threshold signal and to a second fuel mixture for generating a voltage signal having an amplitude less than a predetermined second voltage threshold signal, the method comprising the steps of:

comparing the voltage output of said sensor with the first predetermined voltage threshold signal, generating a first voltage signal when said sensor voltage is equal to said first predetermined voltage threshold signal and maintaining said voltage signal during the period of time when said sensor voltage is less than said first predetermined voltage threshold signal, comparing the voltage output of said sensor with the second predetermined voltage threshold signal, generating a second voltage signal when said sensor voltage is equal to said second predetermined voltage threshold signal and maintaining said voltage signal during the period of time when said sensor voltage is less than said second predetermined voltage threshold signal;

storing said first voltage signal as a third voltage signal having an amplitude proportional to the duration of said first voltage signal;

generating a timing signal from said first voltage signal;

comparing said timing signal with said second voltage signal and generating a storage reset signal if both of said signals are coincident and then generating an alarm whenever said third voltage signal reaches a predetermined voltage magnitude between successive storage reset signals.

10. A system for detecting when the switching rate of the output signal from an electrochemical transducer is within a predetermined time period, said system comprising:

electrochemical transducer generating an output signal having a first voltage level in response to a first chemical mixture and a second voltage level in response to a second chemical mixture;

means for generating a first voltage threshold level intermediate said first and second voltage levels of said transducer output signal;

means for generating a second voltage threshold level intermediate said first voltage threshold level and said second voltage level of said transducer output signal;

means responsive to said transducer output signal changing from said first voltage level to said second voltage level crossing said first voltage threshold level for generating a pulse electrical signal indicating a predetermined switching rate of said transducer output signal between said first and second threshold levels; and a comparator means responsive to said pulse electrical signal from said last mentioned means and said transducer output signal crossing said second voltage threshold level for generating an output signal when the switching rate of said transducer output signal is within the predetermined time period.

* * * * *